(12) United States Patent
Legay

(10) Patent No.: US 8,818,506 B2
(45) Date of Patent: *Aug. 26, 2014

(54) DETECTION OF STRONG STATIC MAGNETIC FIELDS AND MRI EXAMINATION SAFEKEEPING FOR AN IMPLANTABLE CARDIAC PROSTHESIS

(71) Applicant: Sorin CRM S.A.S., Clamart Cedex (FR)

(72) Inventor: Thierry Legay, Fontenay les Briis (FR)

(73) Assignee: Sorin CRM S.A.S., Clamart Cedex (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/049,061

(22) Filed: Oct. 8, 2013

(65) Prior Publication Data
US 2014/0039568 A1 Feb. 6, 2014

Related U.S. Application Data

(63) Continuation of application No. 12/684,798, filed on Jan. 8, 2010, now Pat. No. 8,554,318.

(30) Foreign Application Priority Data
Jan. 9, 2009 (FR) ..................................... 09 00059

(51) Int. Cl.
*A61N 1/16* (2006.01)
(52) U.S. Cl.
USPC .............................................. 607/11; 607/63
(58) Field of Classification Search
USPC ..................................................... 607/11, 63
See application file for complete search history.

(56) References Cited

U.S. PATENT DOCUMENTS

| 6,580,947 B1 * | 6/2003 | Thompson ...................... 607/30 |
| 8,554,318 B2 * | 10/2013 | Legay ............................. 607/11 |
| 2003/0144705 A1 | 7/2003 | Funke |
| 2007/0191914 A1 * | 8/2007 | Stessman ........................ 607/63 |
| 2008/0154342 A1 * | 6/2008 | Digby et al. .................... 607/63 |
| 2010/0308830 A1 | 12/2010 | Shankar et al. |

FOREIGN PATENT DOCUMENTS

| EP | 0 530 006 | 3/1993 |
| EP | 530006 A1 * | 3/1993 |
| EP | 1 935 450 | 6/2008 |
| FR | 2805999 | 9/2001 |
| WO | WO-94/12238 | 6/1994 |
| WO | WO-01/62142 | 8/2001 |
| WO | WO-03/037429 | 5/2003 |
| WO | WO-2006/124481 | 11/2006 |

OTHER PUBLICATIONS

Preliminary Search Report for French Patent Application No. 0900059, dated Jul. 2, 2009, 2 pages.

* cited by examiner

*Primary Examiner* — Christopher D Koharski
*Assistant Examiner* — Michael Carey
(74) *Attorney, Agent, or Firm* — Foley & Lardner LLP

(57) ABSTRACT

An implantable medical device detects a strong static magnetic field associated with an MRI imaging instrument and operates in a safekeeping operating mode. The device includes an electronic circuit for the detection/stimulation of a cardiac activity, a weak field sensor detecting the presence of a first magnetic field of a permanent magnet being located in proximity to the device, a strong field sensor detecting the presence of a second magnetic field of an MRI imaging instrument during the course of an MRI examination.

20 Claims, 1 Drawing Sheet

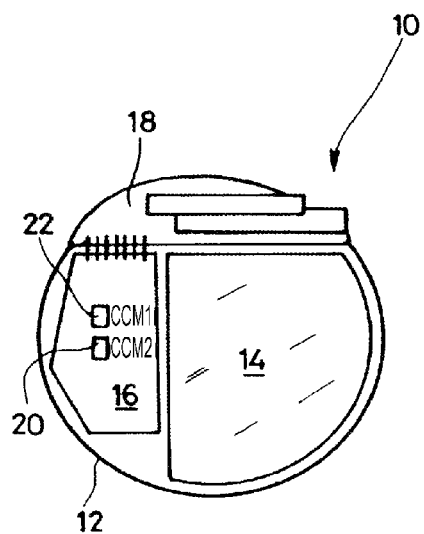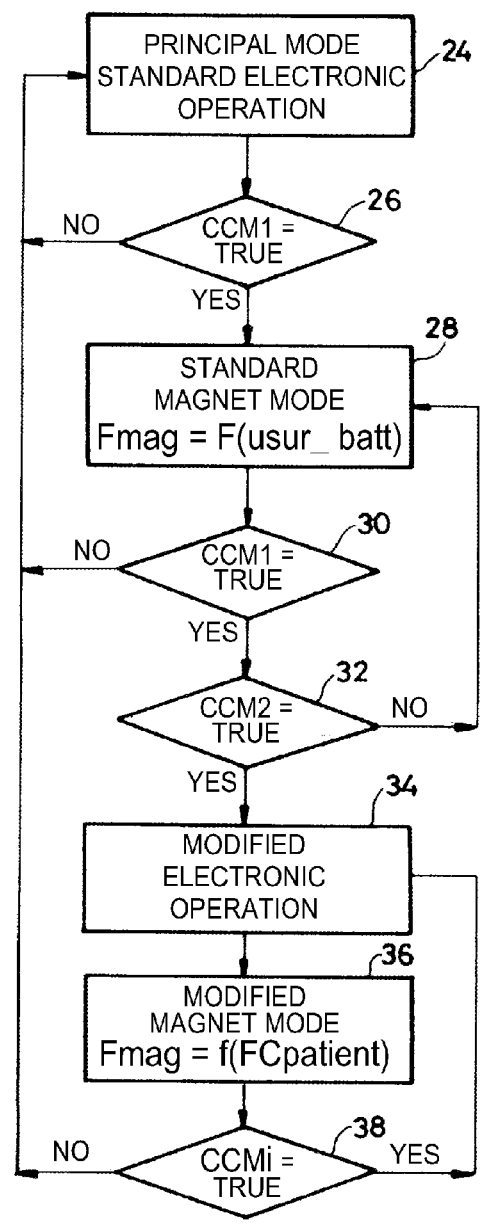

DETECTION OF STRONG STATIC MAGNETIC FIELDS AND MRI EXAMINATION SAFEKEEPING FOR AN IMPLANTABLE CARDIAC PROSTHESIS

CROSS-REFERENCE TO RELATED PATENT APPLICATIONS

The present application is a continuation of U.S. patent application Ser. No. 12/684,798, filed Jan. 8, 2010 and granted as U.S. Pat. No. 8,554,318 on Oct. 8, 2013, which claims the benefit of and priority to French Patent Application No. 0900059, filed Jan. 9, 2009, now abandoned. U.S. patent application Ser. No. 12/684,798 and French Patent Application No. 0900059 are both incorporated herein in their entireties.

BACKGROUND

The present invention is directed to "active implantable medical devices" as defined by the 20 Jun. 1990 Directive 90/385/EEC of the Council of European Communities, more particularly to devices that continuously monitor a patient's heart rhythm and deliver to the heart, if necessary, a resynchronization and/or a defibrillation electrical stimulation pulse, in response to a detected arrhythmia, and even more particularly to the safekeeping (i.e., protection) of such devices from the adverse effects of strong magnetic fields as produced, for example, during a magnetic resonance imaging (MRI) examination.

The active implantable devices associated with the present invention typically include a housing, generally designated as a "generator", that is electrically and mechanically connected to one or more leads. The leads are equipped with electrodes that are intended to come into contact with the patient's myocardium at those sites where the electrical potentials are detected (collected) and/or the stimulation pulses are delivered (applied). These electrodes can be endocardial electrodes (e.g., electrodes that are placed in a cavity of the myocardium in contact with the wall of the myocardium), epicardial electrodes (e.g., electrodes that are preferably used to define a reference potential, or to apply a shock stimulation pulse), or intravascular electrodes (e.g., electrodes that are introduced into the coronary sinus and advanced to a position that faces the myocardial wall of the left ventricle).

Heretofore, an MRI examination was contraindicated for patients having an implanted cardiac pacemaker or defibrillator. This is for several reasons, including, for example:

heating near the electrodes connecting the generator to the patient's heart;

forces and torques of attraction exerted on the device immersed in high intensity magnetic fields generated by an MRI equipment; and unpredictable behavior of the device itself, due to exposure to extreme magnetic fields.

Regarding the unpredictable behavior of a device when exposed to magnetic fields, there have been a number of solutions that resolve this problem. It is indeed desirable that when exposed to static and alternating electromagnetic fields that are generated by a conventional MRI examination, the device behavior is predictable and known in advance. The following problems are likely to occur in such a situation:

an erratic detection of a static electromagnetic field generated during an MRI examination, especially for a device equipped with a Reed magnetic switch. A Reed magnetic switch detects the presence of a permanent magnet in proximity to the device, normally used by a practitioner after implantation to put the device in a safe operating mode, for example, when using an electric scalpel, or to evaluate the state of the battery charge depletion of a device (in a magnet mode, the stimulation frequency is fixed and reflects the level of battery charge). A Reed magnetic switch detects a static electromagnetic field of a relatively low amplitude, but has a totally unpredictable behavior in an MRI environment where the magnetic field is typically stronger by a thousand times than that of a permanent magnet;

the deterioration of its intrinsic performance; and the dynamic signals emitted by the MRI instrument can be detected by the device and misinterpreted as cardiac signals.

In this latter regard, it is necessary to take into account the fact that throughout the duration of an MRI examination—which can last several minutes—the device shall nevertheless remain functional and provide if necessary seamless stimulation of the myocardium.

It is therefore necessary to have means of detection and of management of such a situation, providing the following functions:

indicating to the device that the patient will be subjected to MRI magnetic fields;

inhibiting the circuits of the device that may be disturbed by the electromagnetic fields emitted by the MRI instrument; and operating the device in a dedicated pacing mode, tailored to the patient and compatible with the electromagnetic fields produced by the MRI instrument.

The present invention relates more particularly to the solution to the first function. The second and third solutions may be implemented independently or in combination with the first function.

A first known approach involves an external programmer to indicate to the device that it will be exposed to electromagnetic fields of an MRI instrument and should therefore adopt a particular configuration, both for its own operation and for the delivered stimulation. The difficulty of this approach is that it requires a programmer prior to the test, and thus it requires interruption by a qualified practitioner. In addition, the device needs to be reprogrammed to its original pacing mode after the MRI examination. Otherwise, the patient could leave the MRI center with a device operating in a mode that is not configured for everyday life. Thus, this technique suffers from the pervasive risk that the MRI center fails to reprogram the device before the patient leaves.

Another known approach in the art is to equip the device with means for automatically detecting a magnetic field. As described above, implantable cardiac devices are typically equipped with a detector of a weak magnetic field (also referred to herein as a "weak field"), sensitive to the presence of a magnet (e.g., a permanent magnet) placed near the device to place it in a "magnet mode". Commonly used detectors of weak fields use a Reed magnetic switch. A Reed magnetic switch is too large and unpredictable in the presence of a strong static field of the MRI type. Other types of commonly used detectors of weak fields are integrated sensors such as MAGFET type components described e.g. in international published application WO 94/12238 A1 (which have the disadvantage of consuming energy to operate), or micro electromechanical sensor (MEMS) devices, as is described, e.g., in published French application FR 2 805 999 A1.

These various sensors used to detect a weak field (typically about 1.5 mT) are unsuitable for detecting strong fields such as those produced by MRI instruments (typically between 0.5

T and 3 T or more) which are nearly a thousand times stronger, and are located in areas where ensor may be "deaf" to the presence of a strong field.

Special techniques have been proposed to detect the strength of a static magnetic field of conventional sensors present a non-linear response. Indeed, a weak field s an MRI type. The U.S. Published Application 2007/191914 A1 describes a device detecting the presence of a strong static magnetic field by analyzing the impedance of an inductive component, such as a coil of an inductive switching regulator: the presence of a strong magnetic field has the effect of saturating the core of the inductive component, causing a change in impedance that is detected by the device.

International Published Application WO 2006/124481 A2 describes a technique of detecting the presence of an MRI field by measurement of the voltage collected by the terminals of a telemetry antenna as well as on a lead.

These devices, however, cannot overcome the difficulties outlined above, especially with the high degree of reliability required for an implanted device intended to fully and automatically operate in a strong electromagnetic field.

Published European Application EP 1 935 450 A1 describes another technique of using giant magnetic resistive type (GMR) devices associated in a Wheatstone bridge. The Wheatstone bridge plays the role of a single strong/weak field mixed sensor: indeed, the balance of the bridge is more or less altered by the strength of an electromagnetic field, and changes of the electromagnetic field resulting from the differential voltage are analyzed by a converter placed at the output of the Wheatstone bridge to give an overall estimate of the field level.

SUMMARY

It is, therefore, an object of the present invention to provide for an automatic detection of an electromagnetic field in active implantable medical devices and thereby placing the device, more particularly the circuits used to detect cardiac activity and deliver stimulation pulses to a patient's heart, in a safekeeping (protected) mode of operation in response to the detected electromagnetic field, and allowing the device to automatically exit the safekeeping mode and return to normal (pre electromagnetic field detection) operation when it detects the disappearance of the electromagnetic field.

Yet another object of the present invention is to ensure separation between a detected weak field (e.g., caused by a permanent magnet type) and a strong field (e.g., caused by an MRI instrument) and take appropriate action in either case, placing the device in separate safekeeping modes accordingly tailored to the determined situation.

According to one embodiment, the present invention concurrently implements two sensors of different sensitivity, a first sensor having a higher sensitivity (e.g., to detect weak fields) and a second sensor having a lower sensitivity (e.g., to detect strong fields). The second sensor may be conditionally activated only upon the first sensor detecting a weak field.

Then, after the second sensor detects a strong field, the device is placed in a first safekeeping mode that makes its relevant components insensitive to a strong electromagnetic field such as the one produced by an MRI instrument. This first safekeeping mode of operation is different from the conventional "magnet mode" to better adapt the device to the particular situation of the patient, e.g., undergoing an MRI examination.

Broadly, the present invention is directed to an active implantable medical device of a known type comprising: an electronic circuit for the detection/stimulation of a cardiac activity, a weak field sensor detecting the presence of a magnetic field of a level corresponding to that of a permanent magnet positioned in proximity to the device, means for detecting a strong electromagnetic field including a strong field sensor, the strong field sensor being different from the weak field sensor and detecting the presence of a magnetic field positioned in proximity to the device of a level corresponding to that issued by an MRI imager during an MRI examination, and means for safekeeping of the device to place at least the electronic circuit in an MRI protected mode.

In a preferred embodiment, the device includes means for selective activation of the strong field sensor, operating in response to the weak field sensor and activating the strong field sensor only on detection of a magnetic field by the weak field sensor, and means for MRI safekeeping, placing the electronic circuit in said specific safekeeping operating mode only when both the strong and weak field sensors detect the presence of a magnetic field.

According to one embodiment, the strong field sensor detects the presence of a magnetic field of a level of at least 0.25 T and the weak field sensor detects the presence of a magnetic field of at least 1 mT. In a preferred embodiment, the strong field sensor is a powered sensor, which is conditionally fed energy on detection of a magnetic field by the weak field sensor, for example, a MAGFET type integrated sensor. The weak field sensor may include a coil whose core saturates in the presence of a weak magnetic field, a giant magnetic resistance (GMR) device, or a Hall effect sensor.

According to one embodiment, the means for safekeeping operates as follows:
  upon detection of a magnetic field by the weak field sensor, the device is put into a standard safekeeping (protected) operation mode of a magnet mode type without detection of cardiac activity, and activates the strong field sensor; and
  upon detection of a magnetic field also by the strong field sensor, the electronic circuit and other components of the device that are sensitive to the deleterious effects of exposure to the electromagnetic fields and radio frequency signals emitted by the MRI instrument are inhibited, and at least one parameter of said operation mode of a magnet mode type is modified.

The magnet mode may notably include a mode in which the electronic circuit of detection/stimulation produces stimulation pulses at a first predetermined frequency, depending on the energy charge level of the battery power supply of the device, while the modified magnet mode can be a mode in which the electronic circuit of detection/stimulation produces stimulation pulses at a second predetermined frequency, independent of the charge level of the battery power supply of the device.

According to one embodiment, the second predetermined frequency is determined as a function of the previous average heart rate before the detection of the presence of a magnetic field by both strong and weak field sensors. The second predetermined frequency may be increased above the previous average heart rate.

BRIEF DESCRIPTION OF THE DRAWINGS

Further features, characteristics, and advantages of the present invention will become apparent to a person of ordinary skill in the art from the following detailed description of embodiments of the present invention, made with reference to the annexed drawings, in which:

FIG. 1 is a schematic view of an implanted device generator in accordance with a preferred embodiment of the present invention; and FIG. 2 is a flow chart illustrating a process for carrying out a preferred embodiment of the present invention.

DETAILED DESCRIPTION

As regards to its software aspects, the present invention can be implemented by an appropriate programming of the controlling software of a known device, for example, a cardiac pacemaker, and a resynchronizer and/or defibrillator type device, including means for acquiring a signal provided by endocardial leads and/or one or more implanted sensors.

The adaptation of these devices to implement the functions of the invention as described herein is believed to be within the abilities of a person of ordinary skill in the art, and therefore will not be described in detail.

The invention may particularly be applied to implantable devices such as those of the Reply and Paradym brand device families produced and marketed by Sorin CRM, Clamart, France (formerly known as ELA Medical, Montrouge, France). These devices include programmable microprocessor circuitry to receive, format, and process electrical signals collected (detected) by electrodes implanted and deliver pacing pulses to these electrodes. It is possible to transmit by telemetry software that will be stored in a memory of the implantable devices and executed to implement the functions of the invention that are described herein.

With reference to the drawings, in FIG. 1, reference 10 generally designates a generator of an implantable device, for example, a pacemaker. It should be understood that such an implantable device is merely exemplary and non-limiting of the scope of the invention to active implantable medical devices more generally.

The device 10 includes a housing 12 containing a battery 14 and an electronic circuit 16 connected to a connector 18. Connector 18 may be connected to one or more sensors equipped at their other termination, i.e., the distal termination, by electrodes used for the detection and/or stimulation of a cardiac activity, in a conventional and known manner.

In accordance with an embodiment of the present invention, the device 10 is provided with two magnetic field sensors 20 and 22 implementing circuitry to detect static fields of different intensities.

A first sensor 22, hereinafter referred to as CCM1, is a weak magnetic field sensor (typically, a weak field is in the order of millitesla). Its technology may be one of those commonly used for the detection of a permanent magnet placed near (in proximity to) the device 10 in order to place it in a magnet mode. For this technology choice, one will preferably not use a Reed hermetic switch sensor that includes metal elements because the behavior of such a Reed hermetic switch sensor is unpredictable in the presence of a strong field. The sensor CCM1 may be chosen from among one of the following types of components: a coil whose core saturates in the presence of a weak magnetic field, a giant magnetic resistance (GMR) device, a Hall effect sensor, etc. The sensor CCM1 may already be present in the device and thus can be used without any hardware change.

The second sensor 20, hereinafter referred to as CCM2, is a strong field sensor and does implicate the use of an additional sensor. One suitable device for CCM2 is a silicon sensor of the MAGFET type that is directly integrated into the electronic circuit 16. Therefore, it can be implemented without a significant loss of available space on the electronic circuit 16.

The MAGFET device is a MOS field effect transistor with multiple drains. The area of inversion in the transistor channel created by the polarization is used as a zone of deflection of the carriers during the application of a magnetic field perpendicularly to the plane of the channel. Preferably, the MAGFET is created from an N-type MOS because their greater mobility improves sensitivity. The sensitivity is also a function of various geometric parameters such as the distance between the two drains, the length and width of the channel, and also depends on the conditions of electric polarization.

The sensor CCM2 may include one or more of these MAGFET devices associated with a current detection system to convert the magnetic field in a signal to an electrical quantity such as current, voltage, or frequency. Such a MAGFET type sensor has a particularity of consuming energy to operate, and its sensitivity is relatively low (a variation in the order of several percent per tesla). This makes it particularly well suited to the detection of a high magnetic field, typically fields above 250 mT, more preferably about 0.5 to 3 T or more.

The device 10 in accordance with one embodiment of the present invention includes two field sensors:
 a weak static magnetic field sensor CCM1, typically greater than or equal to 1 mT, and
 a sensor CCM2 reacting only to strong static fields, typically greater than 0.25 T.

With reference to FIG. 2, a preferred method employing the two field sensors will now be described. In the beginning, the device 10 is in a standard non-modified (defined as normal) operating mode (stage 24). If the weak field sensor CCM1 detects a field and in response outputs a signal at or above a threshold True indicating that a weak field has been detected (test 26), then the device goes into a magnet mode (stage 28). The magnet mode operation is well known in the art, and hereinafter exchangeably referred to as a magnet mode or a standard magnet mode. It is employed mainly to stimulate the patient's heart in a conventional DOO pacing mode with a stimulation frequency determined by the charge level of the battery. The magnet mode is thus used to test the charge depletion level of the device power supply, and estimate the remaining life for the device.

In addition, if the strong field sensor CCM2 detects a field and outputs a signal that is at or above a threshold True indicating that a strong field has been detected (test 32), then the operation of the device is modified in a manner explained below (stages 34 and 36).

However, if only sensor CCM2 outputs a signal at or above the threshold True while the weak field sensor CCM1 does not, then it is considered an artifact detected by the sensor CCM2, and no changes are made in the functioning of the device.

The sensor CCM2 is therefore scrutinized only if the sensor CCM1 has already detected a field: this principle allows, advantageously, reducing the power consumption in electronic circuit 16 by connecting the electronics of the strong field sensor CCM2 only if the weak field sensor CCM1 has already given a positive result and detected a field.

If both the CCM1 and CCM2 sensors simultaneously detect a magnetic field, then it is interpreted that there is presence of a field, for example associated with an MRI equipment. The device 10 is placed in a modified magnet mode (stage 36) adapted to this situation.

Advantageously, in the modified magnet mode, the stimulation frequency is no longer indexed to the level of battery charge depletion (as in a standard magnet mode), but rather is indexed to an average patient heart rate, more specifically to the previous value averaged over a number of cardiac cycles and is slightly increased by a fixed value (e.g., 10 bpm) or by a percentage (e.g., 10%); the slight increase in the stimulation heart rate is adopted to ensure a non-competition of the stimulated rhythm (permanent) with the patient's spontaneous rhythm.

A safekeeping mode operation is thus obtained by inhibiting the normal cardiac detection function to avoid detection of an electromagnetic field during an MRI imaging, but keeping a safety margin for a safe stimulation of the patient (unlike in a standard magnet mode).

Additional changes may be made in the operation of the device 10 when it is placed in a modified magnet mode as follows (stage 34):

in the case of an implantable defibrillator, the delivery of shocks is prohibited throughout the duration of an MRI examination; and a number of electronic circuits are disabled directly or indirectly using the magnetic properties of the device, especially an RF telemetry circuit and/or a switching power supply. The power supply is based on a linear voltage regulator or on a capacitive converter, consuming relatively more energy, but advantageously is insensitive to the effects of the magnetic fields.

The modified magnet mode is maintained throughout an MRI examination. The end of the MRI examination is detected (test 38) by the state change of one or the other or both of the sensors CCM1 or CCM2 as follows:

if the weak field sensor CCM1 is used for detecting the state change, the return to normal operation occurs when no more static magnetic field, even small, is detected by the device. It indicates that the patient emerged from the examination room where the MRI imager is located; and if the strong field sensor CCM2 is used for detecting the state change, the return to normal operation occurs earlier, when the patient is removed from the tube of the MRI imager. However, because the sensor CCM2 is used throughout the duration of the MRI examination, the energy consumption of the device is increased due to the MAGFET powered to work.

It should be understood, however, that the safekeeping configuration may be used not only for MRI, but also as a protection in a variety of other electromagnetic environments created by medical devices such as electric scalpels, electrical stimulation devices for transcutaneous nerve stimulation (TENS), as well as equipments of everyday life such as anti-theft gates, electronic article surveillance(EAS) system, and the like.

One skilled in the art will appreciate that the present invention can be practiced by other than the embodiments described herein, which are presented for purposes of illustration and not of limitation.

What is claimed is:

1. A method for operating an active implantable medical device, the method comprising:
    determining whether a first magnetic field is detected in proximity to the device using a first sensor;
    determining whether a second magnetic field is detected in proximity to the device using a second sensor;
    wherein the second sensor is activated in response to a determination that the first magnetic field is detected in proximity to the device;
    operating the active implantable medical device in a safe operating mode in response to a determination that both the first magnetic field and the second magnetic field are detected in proximity to the device; and
    wherein the first and second magnetic fields are different.

2. The method of claim 1, further comprising:
    deactivating the second sensor in response to a determination that the first magnetic field is not detected in proximity to the device.

3. The method of claim 2, wherein:
    activating the second sensor comprises connecting a power source to the second sensor; and
    deactivating the second sensor comprises disconnecting the power source from the second sensor.

4. The method of claim 1, further comprising:
    preventing the active implantable medical device from operating in the safe operating mode unless both the first magnetic field and the second magnetic field are detected.

5. The method of claim 1, further comprising:
    inhibiting a component of the active implantable medical device that is sensitive to the second magnetic field in the safekeeping operating mode.

6. The method of claim 1, further comprising:
    operating the active implantable medical device in a magnet operating mode in response to a determination that the first magnetic field is detected and the second magnetic field is not detected; and
    transitioning into the safe operating mode in response to a determination that the second magnetic field is detected when operating in the magnet operating mode, wherein transitioning into the safe operating mode comprises modifying at least one operating parameter of the magnet operating mode.

7. The method of claim 1, wherein determining whether the first magnetic field is detected comprises determining whether a level of the first magnetic field measured by the first sensor exceeds a first threshold value; and
    wherein determining whether the second magnetic field is detected comprises determining whether a level of the second magnetic field measured by the second sensor exceeds a second threshold value;
    wherein the second threshold value is greater than the first threshold value.

8. The method of claim 1, wherein the first magnetic field is associated with a permanent magnet and the second magnetic field is associated with a magnetic resonance imaging device.

9. The method of claim 1, wherein the first magnetic field is a static magnetic field having a level of at least 1 mT and the second magnetic field is a static magnetic field having a level of at least 0.25 T.

10. The method of claim 1, further comprising:
    producing stimulation pulses at a first frequency in response to a determination that the first magnetic field is detected, wherein the first frequency is a function of a level of charge in a power supply for the active implantable medical device; and
    producing stimulation pulses at a second frequency in response to a determination that the second magnetic field is detected, wherein the second frequency is not a function of the level of charge in the power supply for the active implantable medical device.

11. An active implantable medical device comprising:
    a first sensor configured to detect a first magnetic field in proximity to the device;
    a second sensor configured to detect a second magnetic field in proximity to the device; and
    an electronic circuit configured to determine whether the first magnetic field is detected by the first sensor, to determine whether the second magnetic field is detected by the second sensor, and to operate the active implantable medical device in a safe operating mode in response to a determination that both the first magnetic field and the second magnetic field are detected;

wherein the electronic circuit is configured to activate the second sensor in response to a determination that the first magnetic field is detected in proximity to the device; and wherein the first and second magnetic fields are different.

12. The active implantable medical device of claim 11, wherein the first sensor is at least one of: a coil having a core that saturates in the presence of the first magnetic field, a giant magnetic resistance (GMR) device, and a Hall effect sensor.

13. The active implantable medical device of claim 11, wherein the second sensor is a MAGFET type sensor integrated with the electronic circuit.

14. The active implantable medical device of claim 11, wherein the electronic circuit is configured to:
deactivate the second sensor in response to a determination that the first magnetic field is not detected in proximity to the device.

15. The active implantable medical device of claim 14, wherein:
activating the second sensor comprises connecting a power source to the second sensor; and
deactivating the second sensor comprises disconnecting the power source from the second sensor.

16. The active implantable medical device of claim 11, wherein the electronic circuit is configured to:
prevent the active implantable medical device from operating in the safekeeping operating mode unless both the first magnetic field and the second magnetic field are detected; and
inhibit a component of the active implantable medical device that is sensitive to the second magnetic field in the safekeeping operating mode.

17. An active implantable medical device comprising:
a first sensor configured to detect a weak magnetic field having a level exceeding a first threshold value;
a second sensor configured to detect a strong magnetic field having a level exceeding a second threshold value, wherein the second threshold value is higher than the first threshold value; and
an electronic circuit configured to operate the active implantable medical device in a safekeeping operating mode in response to the first sensor detecting the weak magnetic field and the second sensor detecting the strong magnetic field;
wherein the electronic circuit is configured to inhibit a component of the active implantable medical device that is sensitive to the strong magnetic field in the safekeeping operating mode; and
wherein the electronic circuit is further configured to activate the second sensor in response to a determination that the weak magnetic field is detected in proximity to the device.

18. The active implantable medical device of claim 17, wherein the electronic circuit is configured to operate the active implantable medical device in the safekeeping operating mode only when both the weak magnetic field and strong magnetic field are detected.

19. The active implantable medical device of claim 17, wherein the weak magnetic field is associated with a permanent magnet and the strong magnetic field is associated with a magnetic resonance imaging device.

20. The active implantable medical device of claim 17, wherein the electronic circuit is configured to:
produce stimulation pulses at a first frequency when only the weak magnetic field is detected, wherein the first frequency is based on a measured variable and
produce stimulation pulses at a second frequency when both the weak magnetic field and the strong magnetic field are detected, wherein the second frequency is not based on a measured variable.

* * * * *